United States Patent [19]

Erckel et al.

[11] 4,310,665
[45] Jan. 12, 1982

[54] NOVEL STILBENE COMPOUNDS AND PROCESS FOR THE MANUFACTURE THEREOF

[75] Inventors: Rüdiger Erckel, Eppstein; Günter Rösch, Bad Soden am Taunus, both of Fed. Rep. of Germany

[73] Assignee: Hoechst Aktiengesellschaft, Fed. Rep. of Germany

[21] Appl. No.: 191,000

[22] Filed: Sep. 26, 1980

Related U.S. Application Data

[63] Continuation of Ser. No. 36,688, May 7, 1979, abandoned.

[30] Foreign Application Priority Data

May 10, 1978 [DE] Fed. Rep. of Germany ....... 2820322

[51] Int. Cl.³ .................. C07D 405/14; C07D 409/14; C07D 413/14
[52] U.S. Cl. ............................ 542/435; 252/301.27
[58] Field of Search ......................................... 542/435

[56] References Cited

U.S. PATENT DOCUMENTS 3,644,345  2/1972  Siegrist et al. ..................... 542/435
4,142,044  2/1979  Günther et al. ................... 542/435

Primary Examiner—Arthur P. Demers
Attorney, Agent, or Firm—Connolly and Hutz

[57] ABSTRACT

Compounds of the formula

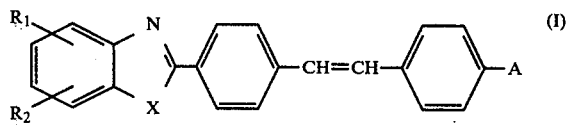

wherein X is O or S, $R_1$ and $R_2$ each are hydrogen, fluorine, chlorine, phenyl, alkyl, alkoxy, dialkylamino, trialkylammonium, acylamino or optionally functionally modified carboxy or sulfo groups, two adjacent radicals $R_1$ and $R_2$ optionally forming together a phenylene, a lower alkylene or a 1,3-dioxapropylene group; and A is a group of the formulae

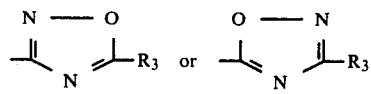

in which $R_3$ is an alpha-, beta- or gamma-pyridyl, pyridyl-methylene, thiophenyl, furanyl, benzofuranyl, pyrazinyl, pyrimidinyl or pyridazinyl group. These compounds, which are suitable as optical brighteners, are prepared by reaction of a compound of the formula

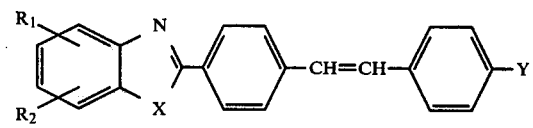

with a compound of the formula

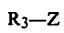

wherein Y is a

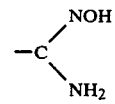

group and Z is —COCl or vice versa.

4 Claims, No Drawings

NOVEL STILBENE COMPOUNDS AND PROCESS FOR THE MANUFACTURE THEREOF

This application is a continuation of application Ser. No. 036,688 filed May 7, 1979 now abandoned.

Subject of the present invention are compounds of the formula I

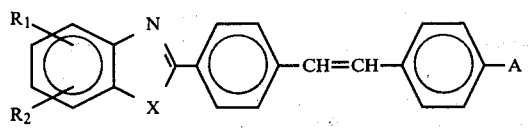 (I)

in which X is O or S; $R_1$ and $R_2$, being identical or different, each are radicals selected from the group of hydrogen, fluorine or chlorine atoms, phenyl, lower alkyl, lower alkoxy, lower dialkylamino, lower trialkylammonium, acylamino groups, or optionally functionally modified carboxy or sulfo groups, two adjacent radicals $R_1$ and $R_2$ optionally forming together a phenylene, a lower alkylene or a 1,3-dioxapropylene group; and A is a group of the formulae

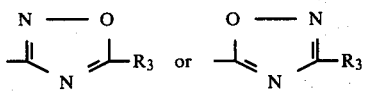

in which $R_3$ is an alpha-, beta- or gamma-pyridyl, pyridylmethylene, thiophenyl, furanyl, benzofuranyl, pyrazinyl, pyrimidinyl or pyridazinyl group.

Especially interesting are those compounds of the formula I, in which A, $R_1$ and $R_2$ are as defined above, X is an oxygen atom and $R_3$ is an alpha-, beta- or gamma-pyridyl, pyridylmethylene, thiophenyl, pyrazinyl, pyrimidinyl or pyridazinyl group.

Preferred are alternatively those compounds of the formula I, in which X is oxygen; $R_1$ and $R_2$ in 5-, 6- or 7-position each are a hydrogen or chlorine atom, ($C_1$-$C_4$)-alkyl, phenyl, or together a fused phenyl ring; and $R_3$ in the A group is an alpha- or beta-pyridyl, thiophenyl, furanyl, benzofuranyl or pyridylmethylene group.

As further subgroups those compounds of the formula I are especially interesting, in which X is an oxygen atom; $R_1$ in 5-position is a hydrogen or chlorine atom, a methyl or phenyl group; $R_2$ is a hydrogen atom; or $R_1$ and $R_2$ each are a methyl group in 5,6- or 5,7-position; and $R_3$ in the A group is an alpha- or beta-pyridyl, thiophenyl, furanyl, benzofuranyl or pyridylmethylene group.

Apart from these subgroups, any further subgroups may be formed by correspondingly combining the individual groups etc. as defined sub X, $R_1$, $R_2$, A and $R_3$. Of course, by formation of such new subgroups it is not intended to introduce new matter according to 35 U.S.C. 132.

By "functionally modified carboxy or sulfo groups", there are to be understood cyano, carboxylic acid ester, carboxylic acid amide, mono- and dialkylcarbonamide, sulfonic acid ester or mono- or dialkylsulfonamide groups.

In detail, the following radicals may be used for $R_1$ and $R_2$: methyl, ethyl, n- or i-propyl, n- or i-butyl, pentyl, hexyl, methoxy, ethoxy, propoxy, butoxy, pentoxy, hexoxy, dimethylamino, diethylamino, trimethylammonium, triethylammonium, acetylamino, cyano, —$SO_3H$, carboxyl, carbomethoxy, -ethoxy, -propoxy, -butoxy and the corresponding groups in the series of sulfonic acid alkyl ester groups, methyl-, ethyl-, propyl-, butyl-carbonamide and the corresponding groups in the series of alkylsulfonamides, or the corresponding dialkylcarbonamide or -sulfonamide groups. Two adjacent $R_1$ and $R_2$ groups may furthermore form a fused phenyl or cyclohexyl ring. Sub the symbol X, all those compounds are preferred which contain the benzoxazolyl group (X=O).

Subject of the invention is furthermore a process for the manufacture of compounds of the formula I, which comprises reacting a compound of the formula II

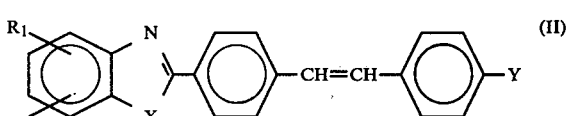 (II)

with a compound of the formula III

 (III)

in which formulae $R_1$, $R_2$, X and $R_3$ are as defined above and Y is a group of the formula IV

 (IV)

Z simultaneously being a group of the formula V

 (V), or Y is a group of the formula V and Z is simultaneously a group of the formula IV.

In the first case, compounds of the formula I containing a 1,2,4-dioxazolyl-3 group are obtained, and in the second case, the compounds of formula I contain the 1,2,4-dioxazolyl-5-group. The reaction is preferably carried out in the presence of an acid-binding agent in an inert solvent at a temperature of from 20° to 200° C. Suitable solvents for the reaction are for example chlorobenzene, di- or trichlorobenzene, and especially dimethyl formamide, N-methylpyrrolidone, dimethyl sulfoxide or nitrobenzene. As acid-binding agents, there may be used for example sodium, potassium or calcium carbonate, triethylamine or ethyl-di-isopropylamine.

The compounds of the formula II, in which Y is a group of formula IV, are obtained from the corresponding nitriles by reaction with hydroxylamine, preferably in alcohols or N-methylpyrrolidone. The corresponding nitriles are known from the literature or can be obtained according to known processes (cf. Japanese Pat. No. Sho 42-21013, U.S. Pat. No. 3,577,411, German Offenlegungsschrift No. 20,00,027). For example, the correspondingly substituted benzoxazolylstilbenecarboxylic acid can be converted via the chloride to the amide according to known processes, and the latter one can be reacted likewise according to known methods with an agent splitting off water to yield the nitrile. The starting compounds of the formula II in which Y is a group of the formula IV can alternatively be prepared according to the process indicated in Chem. Rev. 62

(1962) p. 155 et sequ. In analogous manner, the starting products of the formula III where Z is a group of the formula IV can be obtained according to this latter process. Starting compounds of the formula II in which Y is a group of the formula V are obtained in the following reaction steps known to those skilled in the art:

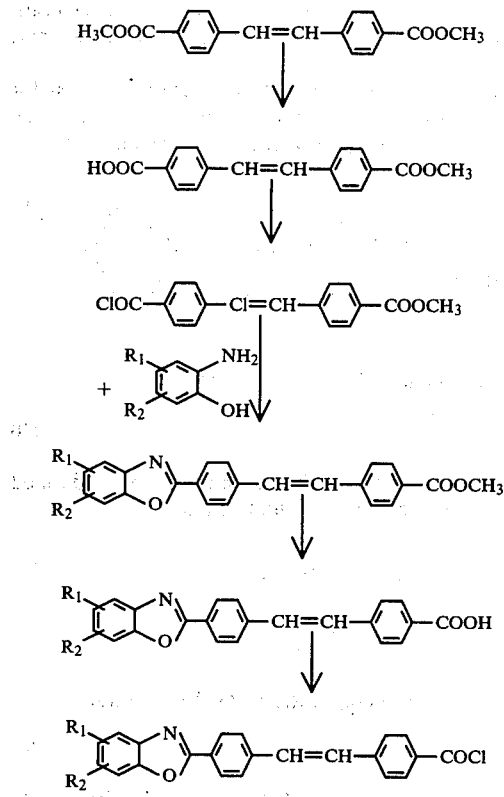

The reaction products of the above processes can be further converted in known manner, for example a reaction starting from sulfo- or carboxy-containing molecules to give functionally modified sulfo or carboxy groups, or conversion of such groups to other groups of this kind or the free acids. Furthermore, chloromethyl groups may be introduced in known manner, methyl groups may be oxidized, or halogenation may be carried out and the halogen atoms introduced may be further converted, for example chlorine or bromine may be replaced by the amine function.

The novel compounds of the formula I are nearly colorless fluorescing substances which are suitable for use as optical brighteners.

Substrates which can be brightened are, for example, the following materials: lacquers, natural and synthetic fibers, for example those of natural or regenerated cellulose, acetyl cellulose, natural or synthetic polyamides, such as wool, polyamide-6 and polyamide-6,6, polyesters, polyolefins, polyvinyl chloride, polyvinylidene chloride, polystyrene or polyacrylonitrile, and sheets, films, ribbons or other shaped articles made from these materials.

The water-insoluble compounds of the present invention may be used in the form of solutions in organic solvents or in aqueous dispersions advantageously with the addition of a dispersing agent. Suitable dispersing agents are for example soaps, polyglycol ethers derived from fatty alcohols, fatty amines or alkylphenols, cellulose sulfite waste liquors or condensation products of optionally alkylated naphthalene-sulfonic acids with formaldehyde.

The compounds of the formula I may also be added to detergents, which may contain the usual fillers and auxiliaries, such as alkali metal silicates, alkali metal phosphates or -polymetaphosphates, alkali metal borates and alkali metal salts of carboxymethylcellulose; foam stabilizers such as alkanolamides of higher fatty acids; or complex-forming agents such as soluble salts of ethylenediamine-tetraacetic acid and diethylenetriamine-pentaacetic acid; or chemical bleaching agents such as perborates and percarbonates.

The brightening of fiber materials with the aqueous or possibly organic brightening liquor may be carried out either according to the exhaust process at temperatures of from preferably 20° to 150° C., or under thermosol conditions, the textile material being impregnated or sprayed with the brightener solution or dispersion, and squeezed between rollers to a residual moisture content of from about 50 to 120%. Subsequently, the textile material is subjected for about 10 to 300 seconds to a heat treatment, preferably dry heat, at temperatures of from about 120° to about 240° C. This thermosol process may be combined with other finishing operations, for example application of synthetic resins in order to obtain easy-care properties.

The compounds of the present invention may also be added to high molecular weight organic materials before or during their processing. They may be added, for example, when manufacturing films, sheets, ribbons or other shaped articles from the corresponding molding compositions, or they may be dissolved in the spinning mass before spinning. Suitable compounds may also be added to the low molecular weight starting materials before the polycondensation or polymerization, such as in the case of polyamide-6, polyamide-6,6 or linear polyesters of the polyethyleneglycol terephthalate type.

Compounds of the present invention which are substituted by one or, preferably, two carboxy or alkoxycarbonyl groups may be linked to linear polyester molecules or synthetic polyamides via an ester or an amide bond when they are added to these materials, or, preferably, their starting substances under suitable conditions. Brighteners anchored in the substrate in this manner by a chemical bond are distinguished by their extraordinary fastness to sublimation and to solvents.

The amount of compounds of the formula I to be used in accordance with this invention, relative to the material to be optically brightened, may vary within wide limits, depending on the field of application and the intended effect, and it may be determined easily by simple tests. Generally it is from about 0.01 to about 2%.

The following Examples illustrate the invention, parts and percentages being by weight unless otherwise stated.

EXAMPLE 1

3.4 g (0.024 mol) of pydridine-4-amidoxime in 100 ml of dimethyl formamide are introduced into the reactor, and 7.2 g (0.02 mol) of 4'-benzoxazolyl-2-stilbene-4-carboxylic acid chloride are added. Subsequently, the mixture is stirred for 1 hour at room temperature, and then refluxed for 2 hours. Suction-filtration is carried out at room temperature, and the filter residue is washed with dimethyl formamide and methanol. After drying, 7.8 g (87.6% of the theory) of the compound having the formula

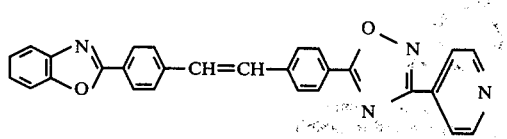

are obtained in the form of a light yellow powder, which, after recrystallization from N-methylpyrrolidone and clarification with animal charcoal has a liquid/crystalline transition temperature of 274°–275° C. and a melting point of 281° C.

Analysis: Calc.: C, 76.0%, H, 4.1%, N, 12.7%; Found: C, 75.8%, H, 4.2%, N, 12.8%. Absorption (in DMF): max=367 nm=74500. Fluorescence (in DMF): max=432 nm.

The pyridine-4-amidoxime used is obtained in the following manner:

70 g (1 mol) of hydroxyammonium chloride in 500 ml of methanol are introduced into the vessel, and a solution of 54 g (1 mol) of sodium methylate in 500 ml of methanol is added. After about 30 minutes, the sodium chloride is filtered off, 41.6 g (0.4 mol) of pyridine-4-carboxylic acid nitrile are added to the filtrate, and the batch is refluxed for 24 hours. Subsequently, the methanol is distilled off, and the residue is recrystallized from 2000 ml of isopropanol with simultaneously clarification with bleaching earth. 49.1 g (89.5% of th., relative to the nitrile used) of pyridine-4-amidoxime having a melting point of 207°–208° C. are obtained which are reacted without further purification.

In analogous manner, the compounds listed in the following Table are obtained.

| No. | R1 | R3 | M.p. (°C.) | max (nm) | ε | Fluorescence (measured in DMF) max (nm) |
|---|---|---|---|---|---|---|
| 2 | CH3 | (pyridyl) | 261–263 | 368 | 75200 | 442 |
| 3 | H | (pyridyl) | 260–262 | 367 | — | 431 |
| 4 | CH3 | (pyridyl) | 270–273 | 369 | 76700 | 483 |
| 5 | H | (thienyl, S) | 261–262 | 367 | 74200 | 431 |
| 6 | CH3 | (thienyl, S) | 251–260 | 368 | 76100 | 436 |
| 7 | H | (pyridyl, N) | 297–298 | 368 | 74700 | 429 |
| 8 | CH3 | (pyridyl, N) | 299–300 | 369 | 76300 | 435 |
| 9 | H | (furyl, O) | 267–268 | 367 | 74700 | 431 |
| 10 | H | (benzofuryl, O) | 273–274 | 367 | — | 433 |

-continued

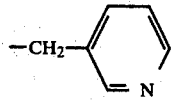

| No. | R₁ | R₃ | M.p. (°C.)* | Absorption (measured in DMF) max (nm) | ε | Fluorescence (measured in DMF) max (nm) |
|---|---|---|---|---|---|---|
| 11 | H | 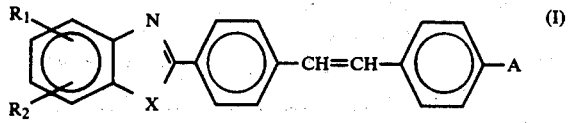 | 260–267 | 366 | 72300 | 428 |

*range of liquid/crystalline transition

What is claimed is:

1. Compounds of the formula I $$R_1, R_2 \text{—phenyl—N=C(X)—phenyl—CH=CH—phenyl—A} \quad (I)$$

in which X is O or S; $R_1$ and $R_2$ are identical or different and each is selected from the group consisting of hydrogen, fluoro, chloro, phenyl, lower alkyl, lower alkoxy, lower dialkylamino, lower trialkylammonium, acylamino, cyano, carboxylic acid ester, carboxylic acid amide, monoalkylcarbonamide, dialkylcarbonamide, sulfonic acid ester, monoalkylsulfonamide and dialkylsulfonamide; or $R_1$ and $R_2$ conjointly are a phenylene, a lower alkylene or a 1,3-dioxapropylene;
and A is a group of the formulae

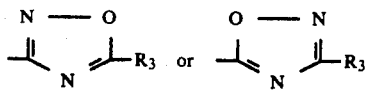

in which $R_3$ is an alpha-, beta- or gamma-pyridyl, pyridylmethylene, thiophenyl, furanyl, benzofuranyl, pyrazinyl, pyrimidinyl or pyridazinyl group.

2. Compounds as claimed in claim 1, wherein A, $R_1$ and $R_2$ are as defined in claim 1, and $R_3$ is an alpha-, beta- or gamma-pyridyl, pyridylmethylene, thiophenyl, pyrazinyl, pyrimidinyl or pyridazinyl group.

3. Compounds as claimed in claim 1, wherein X is oxygen; $R_1$ and $R_2$ in 5- or 7-position each are a hydrogen or chlorine atom, ($C_1$–$C_4$)-alkyl, phenyl, or together a fused phenyl ring; and $R_3$ is an alpha- or beta-pyridyl, thiophenyl, furanyl, benzofuranyl or pyridylmethylene group.

4. Compounds as claimed in claim 1, wherein X is an oxygen atom; $R_1$ in 5-position is a hydrogen or chlorine atom, a methyl or phenyl group; $R_2$ is a hydrogen atom; or $R_1$ and $R_2$ each are a methyl group in 5,6- or 5,7-position; and $R_3$ in the A group is an alpha- or beta-pyridyl, thiophenyl, furanyl, benzofuranyl or pyridylmethylene group.

* * * * *